US006645378B1

(12) United States Patent
Liu et al.

(10) Patent No.: US 6,645,378 B1
(45) Date of Patent: Nov. 11, 2003

(54) POLAR SILANES AND THEIR USE ON SILICA SUPPORTS

(75) Inventors: Xiaodong Liu, Fremont, CA (US); Andrei V. Bordunov, Campbell, CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

(21) Appl. No.: 10/092,024

(22) Filed: Mar. 5, 2002

(51) Int. Cl.$^7$ ................................................ B01D 15/08
(52) U.S. Cl. ........................... 210/198.2; 210/502.1; 210/635; 210/656; 502/401
(58) Field of Search ........................ 210/635, 656, 210/198.2, 502.1; 502/401, 407

(56) References Cited

U.S. PATENT DOCUMENTS

| | | | | | |
|---|---|---|---|---|---|
| 3,983,299 A | * | 9/1976 | Regnier | .................... | 210/198.2 |
| 4,029,583 A | * | 6/1977 | Ho Chang | ............... | 210/198.2 |
| 4,298,500 A | * | 11/1981 | Abbott | .................... | 210/198.2 |
| 4,746,572 A | * | 5/1988 | Glajch | ........................ | 428/403 |
| 5,137,627 A | * | 8/1992 | Feibush | .................... | 210/198.2 |
| 5,149,426 A | * | 9/1992 | Watabe | .................... | 210/198.2 |
| 5,240,602 A | * | 8/1993 | Hammen | .................. | 210/198.2 |
| 5,277,813 A | * | 1/1994 | Feibush | .................... | 210/502.1 |
| 5,453,186 A | * | 9/1995 | Muller | .................... | 210/198.2 |
| 5,647,987 A | * | 7/1997 | Muller | ........................ | 210/635 |
| 5,869,724 A | * | 2/1999 | Kirkland | .................. | 210/198.2 |
| 6,375,846 B1 | * | 4/2002 | Jarrett | ........................ | 210/635 |

FOREIGN PATENT DOCUMENTS

| | | | | |
|---|---|---|---|---|
| EP | 0 386 926 A2 | 9/1990 | ............... | 210/198.2 |
| EP | 0 579 102 B1 | 1/1994 | ............... | 210/198.2 |

OTHER PUBLICATIONS

Reid, T.S. and Henry, R.A., American Laboratory 24–28 (Jul. 1999).

Majors, R.E., New Chromatography Columns and Accessories at the 2001 Pittsburgh Conference, Part 1, LCGC 19:272–288 (Mar. 2001).

Waters Corporation, "A Review of Waters' Bonded Phase Shield Technology and Its Use in High Performance Liquid Chromatography," (Apr. 2000).

* cited by examiner

Primary Examiner—Ernest G. Therkorn
(74) Attorney, Agent, or Firm—Dorsey & Whitney LLP; David J. Brezner

(57) ABSTRACT

A modified silica support having a polar phase bound to its surface and suitable for use for chromatographic separations, having the following formula:

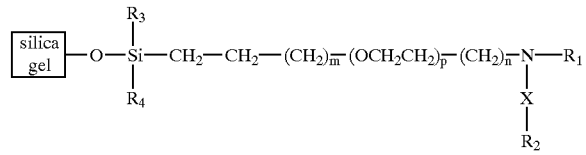

wherein, m=0–20; n=0–20; p=1–50; X is sulfonyl, carbonyl, carbamoyl, or oxycarbonyl; $R_1$=H, alkyl, substituted alkyl, aryl or substituted aryl groups; $R_2$=alkyl, substituted alkyl, aryl or substituted aryl groups; and $R_3$ and $R_4$ are alkyl, aryl, hydroxyl, or alkoxyl groups or groups including oxygen atoms cross-linked to silicon atoms. Also, a polar silane intermediate to make this support.

6 Claims, 6 Drawing Sheets

Figure 3 Polarity Test

Figure 4  Phase Collapse Test

Figure 5 Stability Test

Figure 6 Polar Selectivity

POLAR SILANES AND THEIR USE ON SILICA SUPPORTS

FIELD OF THE INVENTION

The present invention relates to new stationary phases and their use in HPLC (High Performance Liquid Chromatography), LC/MS and other preparative and analytical methods. More particularly, this invention relates to new silanes, their immobilization on silica supports and use of the modified silica supports as stationary phases in liquid chromatography (LC), LC/MS and other preparative and analytical methods.

BACKGROUND OF THE INVENTION

HPLC is widely used to separate analytes in liquid samples. The sample is injected in an eluent into a chromatography column. The sample components are separated by one or more mechanisms including sorption, size exclusion, ion exchange or other interactions with the chromatography packing. The sample components are then detected by any conventional detector, e.g., UV, fluorescence or conductivity.

Silica-based RP (reverse phase) packing materials are commonly used in chromatography columns. They contain unreacted silanol groups on the silica surfaces. Residual silanol sites can interact with polar analytes, especially with basic compounds via ion exchange, hydrogen bonding and dipole-dipole mechanisms. These interactions can create problems ranging from increased retention to excessive tailing and irreversible adsorption of the sample. These undesirable effects can be minimized by using ultra pure silica and maximizing the surface coverage with hydrophobic ligands and endcapping reagents. However, highly aqueous mobile phases are often required to conduct separation of hydrophilic analytes by RP HPLC. Conventional RP C18 columns show a reversible loss of retention when operated under these conditions. The rate and degree of retention loss can vary greatly among different columns. A common explanation for this effect is that the hydrophobic alkyl chains are not wettable and appear to fold down on the silica surface to avoid the exposure to hydrophilic media. In this folded or matted-down state, the alkyl chains have reduced surface area for hydrophobic interaction with the solutes resulting in loss of retention. Reid, T. S.; Henry, R. A., *American Laboratory* 24–28 (July 1999).

In order to achieve the compatibility of RP C18 HPLC columns with highly aqueous mobile phases and to improve the peak shape of basic analytes, polar-embedded phases have been suggested. Majors, R. E., *LC-GC* 19:272–288 (2001). These phases are primarily hydrophobic but have hydrophilic groups incorporated near the silica surface. A benefit of this modification is that the polar-embedded phases exhibit typical reversed-phase behavior with water-organic solvent mixtures and can function well in highly aqueous environment with little or even no organic modifier present. The hydrophilic moieties also can impart different selectivity and retention characteristics compared to conventional reversed-phase materials. Polar-embedded phases have improved tailing characteristics for basic analytes due to shielding effect of the incorporated polar groups on residual silanols. Polar groups mask undesirable silanol activity and prevent hydrophilic analytes from being retained via interaction with underivatized silica surface.

In the early 1990's, conventional C18 and C8 silica stationary phases continued yielding large tailing factors for basic analytes. At that time, several research groups reported a novel type of bonded phases in which a polar functional group was embedded into the alkyl chains. These materials were found to reduce silanol interactions with basic analytes. The most commonly used polar groups were amide, urea, ether and carbamate functionalities.

Early reported materials were prepared by a two-step surface modification. Feibush, B. EP-A-0386926 (1990). In step one, the silica support was bonded with an aminopropyl silane In step two, the amino groups reacted with an acid chloride to form amide linkages. This first generation methodology suffers from poor surface reproducibly over two successive reactions. Functionalized surface has a mixture of derivatized and underivatized amino groups. Therefore, the resulting phases exhibited undesirable ion exchange interactions due to the presence of unreacted basic sites.

Later, materials were prepared by one-step surface modification, where polar functional groups were built into a silane molecule. Neue, U. D.; Niederländer, C. L.; Perterson, J. S., EP-B-0579102 (1993). A single surface reaction with silane yields only one ligand structure with no anion exchange functionality being present.

SUMMARY OF THE INVENTION

One aspect of the invention relates to a modified silica support having a polar phase bound to its surface and suitable for use for chromatographic separations. The modified silica support has the following formula:

wherein, m=0–20; n=0–20; p=1–50;

X is sulfonyl, carbonyl, carbamoyl, or oxycarbonyl;

$R_1$=H, alkyl, substituted alkyl, aryl or substituted aryl groups;

$R_2$=alkyl, substituted alkyl, aryl or substituted aryl groups; and $R_3$ and $R_4$ are alkyl, aryl, hydroxyl, or alkoxyl groups or groups including oxygen atoms cross-linked to silicon atoms.

Another aspect of the invention relates to polar silanes useful as an intermediate in forming the polar phase of the modified silica support. The polar silane has the following formula:

wherein, m=0–20; n=0–20; p=0–50;

X is a sulfonyl, carbonyl, carbamoyl, or oxycarbonyl, provided that p=at least 1 where X is a carbonyl, carbamoyl or oxycarbonyl;

$R_1$=H, alkyl, substituted alkyl, aryl or substituted aryl groups;

$R_2$=alkyl, substituted alkyl, aryl or substituted aryl groups;

$R_3$, $R_4$ and $R_5$ are alkyl, aryl or reactive leaving groups and at least one of $R_3$, $R_4$ or $R_5$ is a leaving group (such as an alkoxyl, halide, hydroxyl or amino group).

DETAILED DESCRIPTION OF THE PREFERRED EMBODIMENTS

The present invention relates to modified silanes and their use in forming modified silica supports. The silica supports have polar phases bound to their surface and are suitable for use in chromatographic separations. In a preferred embodiment, such modified silica supports are useful in reverse phase (RP) chromatography such as described herein in more detail as is well known in the prior art.

The specification will first describe the modified silica support having a polar phase according to the present invention. Then it will describe the polar phase and different methods for making the modified silica support, including methods for making the polar phase.

The modified silica support has the following Formula 1:

(1)

wherein, m=0–20; n=0–20; p=1–50;

X is a sulfonyl, carbonyl, carbamoyl, or oxycarbonyl;

$R_1$=H, alkyl (e.g. C1 to C30), substituted alkyl (e.g. $CH_2OH$), aryl (e.g. phenyl) or substituted aryl (e.g. $CH_2Ph$) groups;

$R_2$=alkyl (e.g. C1 to C30), substituted alkyl (e.g. $CH_2OH$), aryl (e.g. phenyl) or substituted aryl groups (e.g. $CH_2$ phenyl); and $R_3$ and $R_4$ are alkyl, aryl, hydroxyl, or alkoxyl groups or groups including oxygen atoms cross-linked to silicon atoms.

The types of silica supports used in the present invention include any of the known silica support, particularly those used in RP chromatography. Silica supports to be modified are well known in the field. The most common form of silica supports are silica gel particles in a chromatography column.

Referring to Formula (1), in one preferred embodiment $R_1$ and/or $R_2$ are alkyl groups with a carbon chain length of C1 to C30. For use as RP chromatography packing, the alkyl carbon chain of $R_1$ or $R_2$ preferably is of sufficient length to impart a reverse phase property to the modified silica support. Suitable long hydrocarbon chains preferably are in the range of C4–C18, more preferably C10–C16. Also, the modified silica support can include ion exchange, ligand exchange, or hydrophilic properties.

In a preferred embodiment, X is a sulfonyl. Sulfones provide the following advantages: (1) chemical stability in a wide pH range at elevated temperatures and (2) unique selectivity.

Typical values f the substituents are: m=1–3; p=1,2; n 0; $R_3$ and $R_4$=$CH_3$; $R_1$=$C_1$–$C_{18}$; $R_2$=$C_1$–$C_{18}$.

The silane polar phases are bound to the silica, preferably silica gel, in a variety of ways depending upon the types of the silane reagent, silica particles and the desired property of the phases. Standard conditions for silica surface treatment include bonding of the silanes with porous silica (e.g. 60 Å to 2000 Å silica) or non-porous silica particles. The reactions can be carried out in a slurry of silica gel and an inert solvent such as toluene at elevated temperatures. Addition of water or acid or base catalyst can be applied to enhance the surface coverage as is well known. The modified silica supports of the present invention contain aminoalcohols as polar units. The polar silane reagents of the present invention utilize different reaction capabilities of amino and hydroxy groups of the aminoalcohols to derivatize them with hydrocarbon chains at one end and silane functionality at the other end. Then, the silica surfaces are modified by silane ligands containing the polar moieties.

The polar phases embedded in the modified silica support includes a variety of polar-embedded RP materials including ethanolamide and ethanolsulfonamide RP phases. As will be described below, in one preferred embodiment, the method of embedding the polar phase into the silica support can be performed in a single step in which free amino groups are consumed before bonding. This has the advantage of avoiding residual amino groups on the silica surface which could occur if the amines were bound to the surface prior to attachment of the main hydrophobic chain.

In one embodiment, silane is attached to the silica support to form a reversed phase material modified with N-substituted polar functionalities. Such silane ligands suitably have the following Formula 2:

wherein, m=0–20; n=0–20; p=0–50;

X is sulfonyl, carbonyl, carbamoyl, or oxycarbonyl; provided that p=at least 1 where X is a carbonyl, carbamoyl or oxycarbonyl;

$R_1$=H, alkyl, substituted alkyl, aryl or substituted aryl groups;

$R_2$=alkyl, substituted alkyl, aryl or substituted aryl groups;

$R_3$, $R_4$ and $R_5$ are alkyl, aryl or reactive leaving groups and at least one of $R_3$, $R_4$ or $R_5$ is a leaving group.

Molecules produced by Formula 2 where p=0 can be synthesized on a single set sulfonylation process starting either from the corresponding aminosilane and sulfonyl halide or from an unsaturated amine and sulfonyl halide followed by hydrosilylation of the unsaturated group with halide (e.g., chloro) alkoxy or amino silane in the presence of catalyst.

The leaving groups include leaving groups known to those of skill in the art capable of being removed to form a covalent bond through hydroxyl groups on the silica supports. Such leaving groups can include hydroxy, alkoxyl, halides and amino groups, or groups derived from these functionalities.

Aminoalcohols are bi-functional molecules. The different reactivity of amino and hydroxyl groups allows functionalization of both terminals in a sequential manner without applying any protecting groups. One set reaction scheme is illustrated by the following reactions:

Synthesis of N-substituted allyl ethers

Hydrosilylation

Attachment of the polar group to a silica gel may be accomplished as follows:

Endcapping of free hydroxyl groups on the silica gel may be accomplished by the following reaction:

wherein, X, $R_1$, and $R_2$ are defined in Formula 1 above.

Synthesis of the aminoalcohol derived silane ligands and modification of the silica surface with those ligands suitably may be performed in steps (3a)–(3e) as follows:

1. Alkylation of the aminoalcohol, for instance, ethanolamine with alkylbromide. The first reaction of step 3a illustrated as a predominant N-alkylation in presence of the potassium carbonate. Alternatively, $R_1$ can also be introduced upon predominant O-alkylation of the aminoalcohol using stronger bases that deprotonate the hydroxyl group in the presence of the intact amino group (not shown).

2. Introducing an unsaturated moiety, for instance, allyl group via O-alkylation also is illustrated in the second reaction of step 3a. Alternatively, the O-alkylation, unsaturated fragment can be attached via amino group (not shown).
3. Monosubstituted amino groups of the aminoalcohols react with acylating agents, sulfonylating agents, or isocyanates to produce precursors formed in step 3b for hydrosilylation (step 3c).
4. In step 3c, hydrosilylation is performed in the presence of the platinum catalysts with mono, di- or trialkoxy, chloro or amino silanes providing a silane modifying agent for step 3d.
5. In step 3d, the silane modifying agent is attached to the silica gel under reflux in organic solvent such as toluene.
6. In optional step 3e, residual silanol groups are endcapped (e.g. by reaction with alkyl silanes having a leaving group like that of Formula 2).

Long hydrocarbon chain can be a part of either alkylating agent (substituent $R_1$), sulfonylating or acylating reagent (substituent $R_2$) for the synthesis of N-substituted ethanolsulfonamidyl and ethanolamidyl alkyl ethers. For instance, suitably $R_1$=C18, C10 or C16 and $R_2$=CH$_3$ substituents.

Secondary aminoalcohols can be used as starting materials for the synthesis of N-substituted ethanolsulfonamidyl and ethanolamidyl alkyl ethers. In this case, the first step of the reaction sequence (3a) can be avoided and the chain length of the $R_1$ and is $R_2$ substituents can be varied according to reaction scheme (4) which represents an alternative way of introducing hydrophobic chains into ligand structures. For instance, suitably $R_1$=CH$_3$, and $R_2$=C18, C10 or C16 substituents. (4)

wherein, X, $R_1$, and $R_2$ are defined in Formula 1 above.

An exemplary list of suitable N-substituted polar silane ligands for silica surface functionalization includes those listed in the following Table 1.

TABLE 1

7

TABLE 1-continued

8

9

10

11

12

13

14

TABLE 1-continued

An alternative synthesis of an N-substituted allyl ethers is set forth in the following reaction scheme (5).

In scheme (5) X is a carbonyl, sulfonyl, carbamoyl, or oxycarbonyl; $R_1$ and $R_2$=alkyl groups, substituted alkyl groups, aryl groups or substituted aryl groups Further details of the invention are illustrated in the following non-limiting examples.

EXAMPLE 1

General Procedure for the Preparation of New N-substituted Carbamoyl, Sulfonamidyl or Amidylallyl Ethers (Formula 1)

Ethanolamine (400 mmol) was mixed with potassium carbonate (20 mmol) in toluene (1000 mL). Then, the resulting mixture was stirred at 70° C. After 30 minutes of stirring, an alkyl halide (40 mmol) was slowly added to above mixture. The reaction was stirred at 70° C. for 24 hours. Then, all volatiles were removed under reduced pressure and the residue was extracted with $Et_2O/H_2O$. The organic phase was then dried under $Na_2SO_4$ and concentrated under reduced pressure to give corresponding N-substituted amino-ethanol 1 (Reaction Scheme (3a)). The structures of synthesized compounds were confirmed by $^1H$ NMR spectroscopy.

A solution of N-substituted amino-ethanol 1 (20 mmol) in THF (400 mL) was slowly added to a suspension of NaH (22 mmol) in THF (400 mL) at room temperature. Then, the mixture was stirred at 50° C. for 4 hours followed by slow addition of allyl bromide (24 mmol) in THF (50 mL). After stirring at 50° C. for 24 hours, all volatiles were removed under reduced pressure. The residue was dissolved in a mixture of $CH_2Cl_2$ and $H_2O$. The organic phase was further washed with water followed by drying over $Na_2SO_4$. Removal of the volatiles from organic phase yielded allyl ether 2 (Reaction Scheme 3a). The structures of synthesized compounds were confirmed by $^1H$ NMR and Mass spectroscopy.

Substituted allyl ether (15 mmol) 2 (Reaction Scheme 3b) was mixed with $Et_3N$ (30 mmol) in $CH_2Cl_2$ (300 mL) and kept at 0° C. for 20 minutes. Then, a solution of acid chloride, sulfonyl chloride or isocyanate (15 mmol) in CH$_2$Cl$_2$ (50 mL) was slowly added and the reaction mixture was stirred at ambient temperature for 12 hours. The reaction mixture was washed with water and dried over Na$_2$SO$_4$. After removal of all volatiles under reduced pressure, the corresponding N-substituted polar allyl ethers 3 (Reaction Scheme 3b) were obtained. The structures of synthesized compounds were confirmed by $^1$H NMR and Mass spectroscopy.

EXAMPLE 2

General Procedure for Hydrosilylation

N-substituted polar allyl ether 3 (10 mmol) was added to a mixture of mono-, di- or triethoxysilane. Then, a catalyst (0.1 mmol) such as hexachloroplatinic acid in minimum amount of ethanol was introduced. After stirring at 50° C. for 24 hours, the excess of silane and solvent were removed under reduced pressure to yield corresponding N-substituted polar silanes (Table 1). The structures of synthesized compounds were confirmed by $^1$H NMR spectroscopy.

EXAMPLE 3

Silanol Activity

Figure 1:
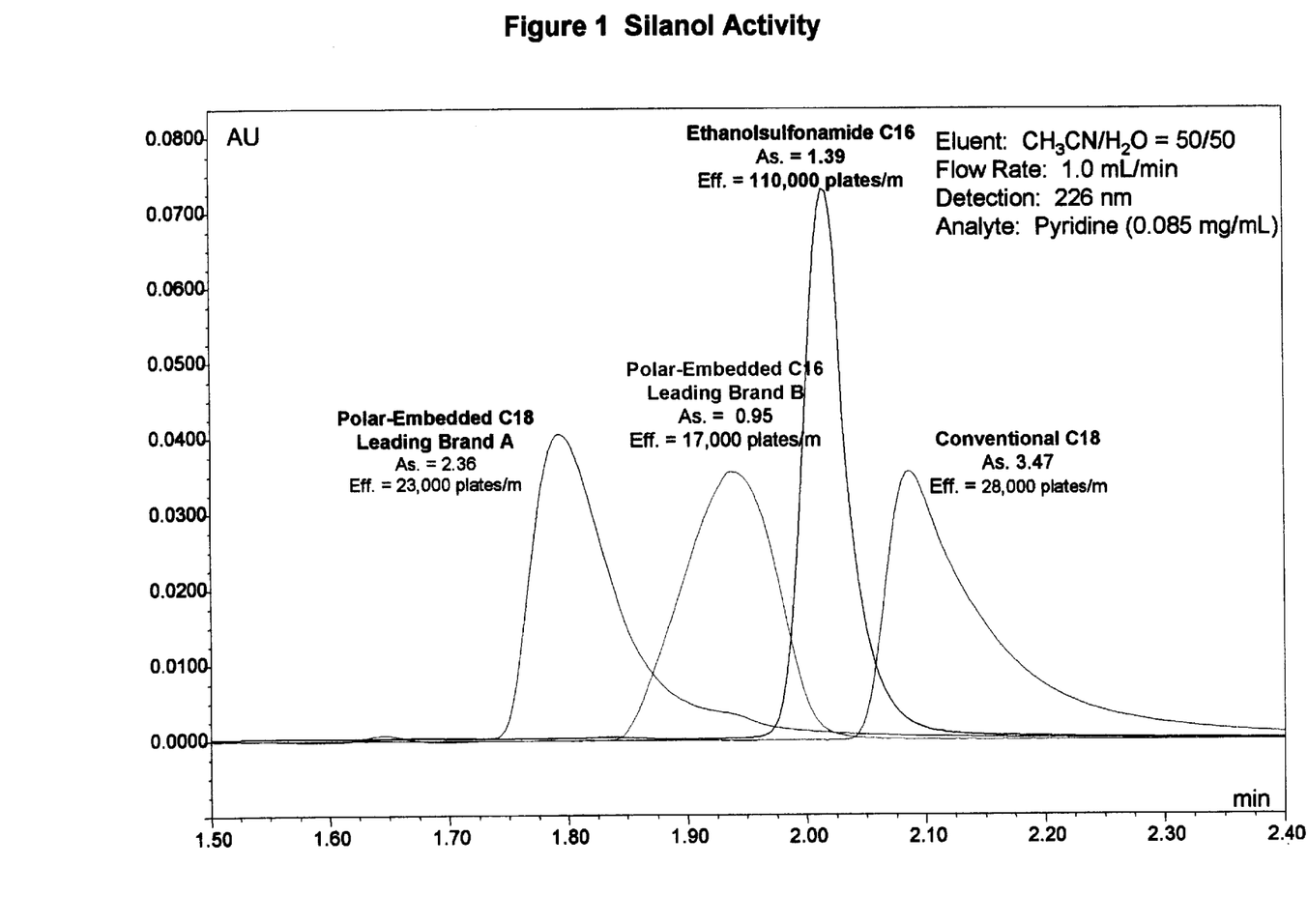
FIG. 1 shows the comparison of silanol activity using developed ethanolsulfonamide C16 column, conventional C18 and two commercial polar-embedded phases A and B. Developed ethanolsulfonamide C16 column exhibits superior efficiency and peak shape.

FIG. 1 shows comparison chromatogramns of pyridine test of the developed ethanolsulfonamide C16 column against a conventional C18 column and two commercial polar-embedded phases A and B. Ethanolsulfonamide C16 column exhibits superior efficiency and peak shape. The test conditions: 30° C., CH$_3$CN/H$_2$O=50/50, 1 mL/min, 5 µL injection volume, 226 nm.

EXAMPLE 4

Amitriptyline Test

Figure 2:
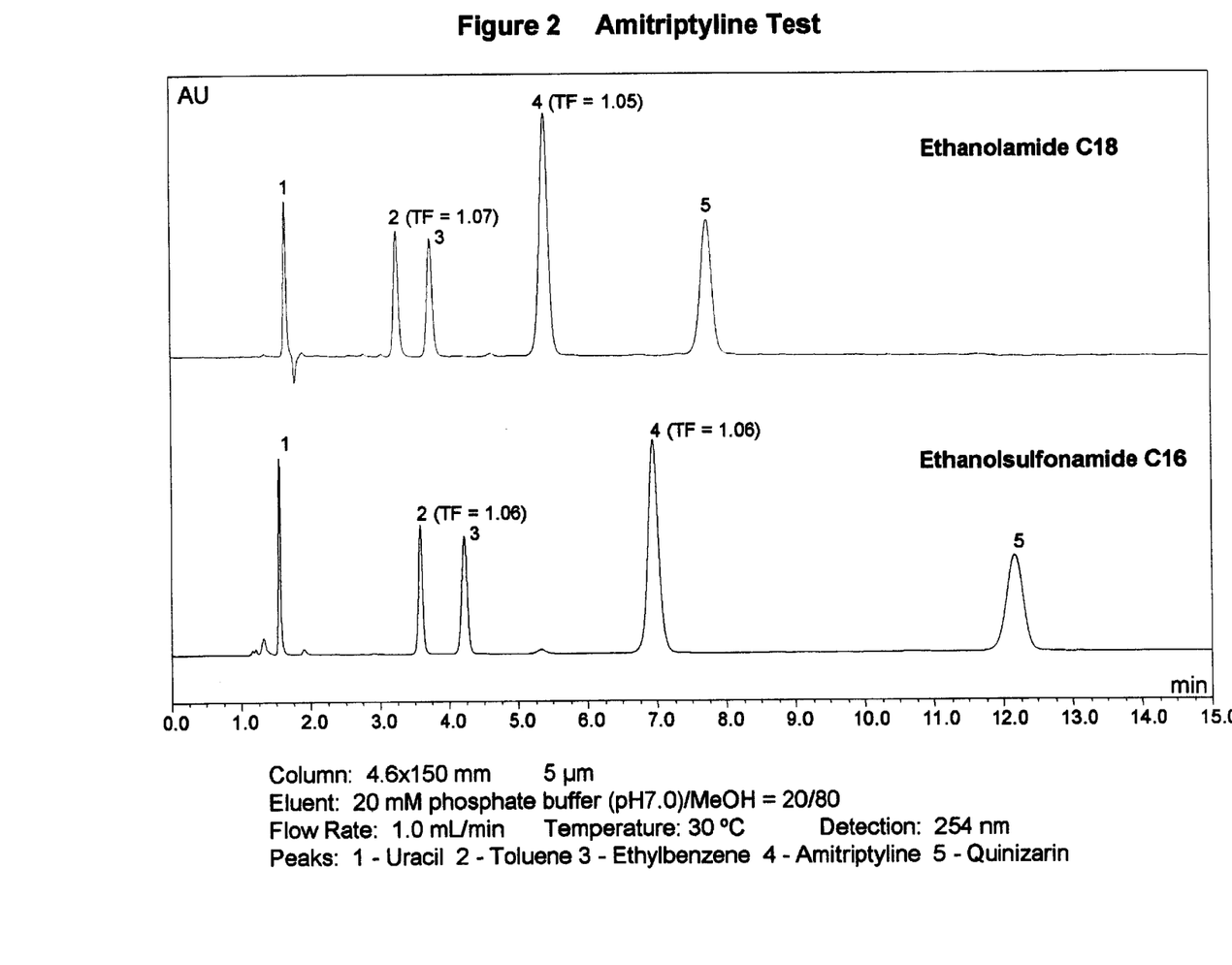
FIG. 2 shows the results of the amitriptyline test using newly developed ethanolsulfonamide C16 and ethanolamide C18 phases. Both phases provide excellent peak shapes.

FIG. 2 shows the test chromatograms of five analytes including amitriptyline on ethanolsulfonamide C16 and ethanolamide C18 phases. Both phases show excellent peak shapes. The test mix contains uracil, toluene, ethylbenzene, amitriptyline and quinizarin. The test conditions: 30° C., 20 mM KH$_2$PO$_4$ 80% MeOH, pH=7.0, mL/min, 5 µL injection volume, 254 nm.

EXAMPLE 5

Polarity Test

Figure 3:
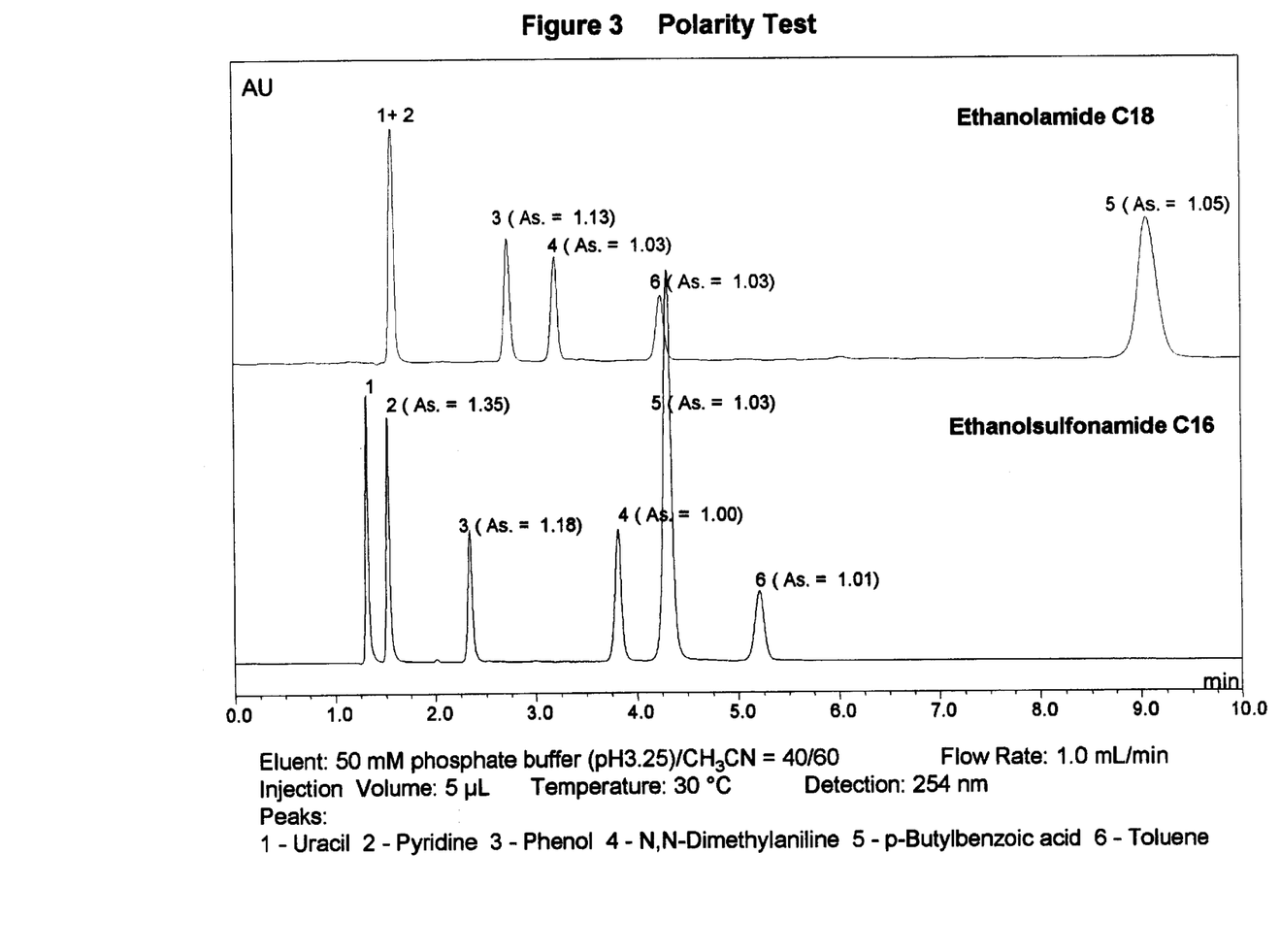
FIG. 3 shows the results of the polarity test using newly developed ethanolsulfonamide C16 and ethanolamide C18 phases. Both phases show excellent peak shapes for acidic (phenol and p-butyl benzoic acid) and basic analytes (pyridine and NN-dimethyl aniline).

FIG. 3 shows the results of the polarity test on the newly developed ethanolsulfonamide C16 and ethanolamide C18 phases. Both phases provide excellent peak shapes for acidic (phenol and p-butyl benzoic acid) and basic analytes (pyridine and NN-dimethyl aniline). The test conditions: 30° C., 50 mM KH$_2$PO$_4$ (pH=3.2)/CH$_3$CN=40/60, 1 mL/min, 5 µL injection volume, 254 nm.

EXAMPLE 6

Phase Collapse Test

Figure 4:
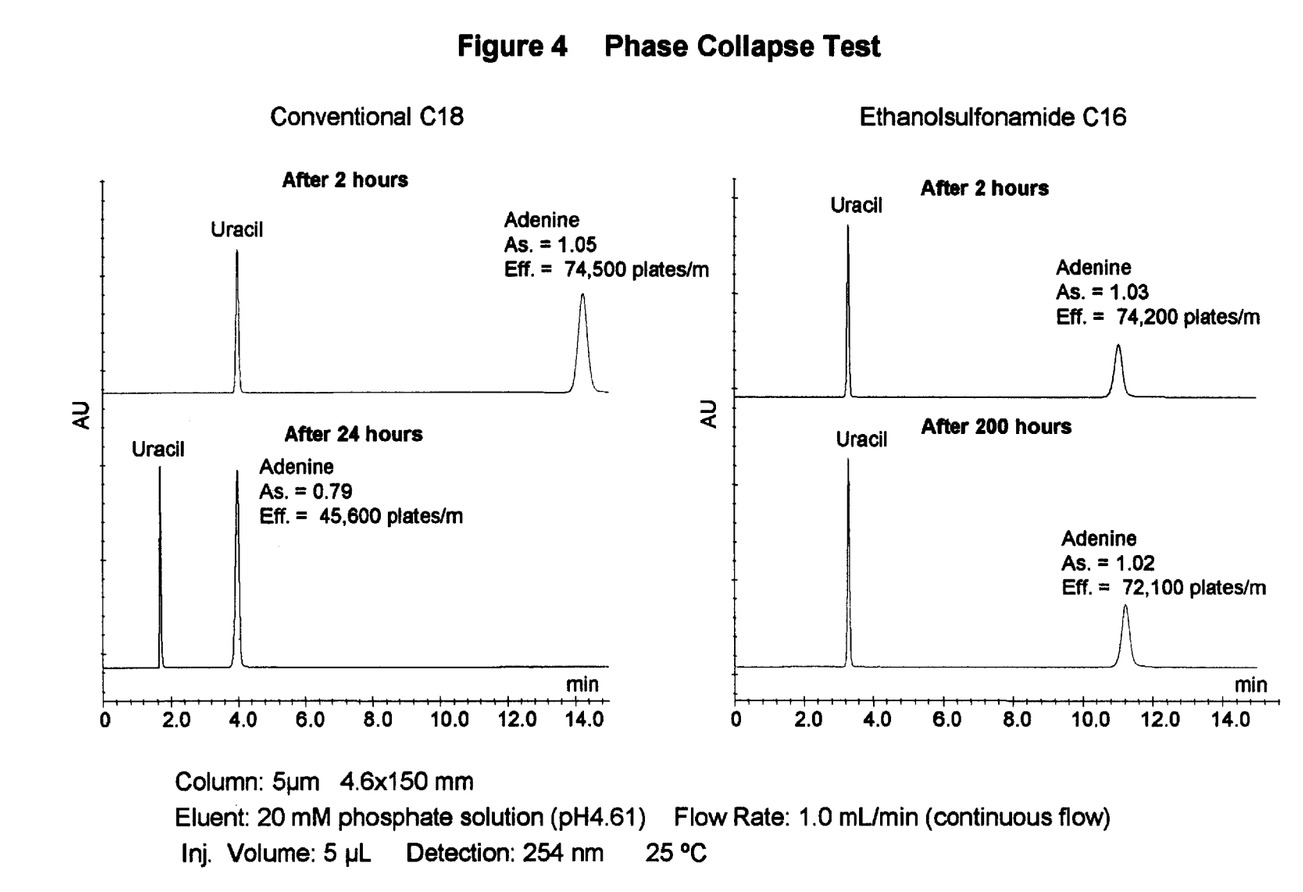
FIG. 4 demonstrates the results of the "phase collapse" test for the developed ethanolsulfonamide C16 phase against conventional C18 column. The ethanolsulfonamide C16 polar phase is immune to a "phase collapse" during 200 hours of continuous exposure to 100% aqueous buffer while the conventional C18 column 5 suffers from significant loss of retention with 24 hours.

FIG. 4 shows the results of the phase collapse test on developed ethanolsulfonamide C16 column in comparison with conventional RP C18 phase using adenine as a probe. After 24 hours exposure to 100% aqueous media, the conventional C18 column suffers from the loss of retention and decrease of the column efficiency. Newly developed sulfonamide C16 phase is immune to pure aqueous conditions after continuous exposure to 100% aqueous buffer for 200 hours.

EXAMPLE 7

Stability Test

Figure 5:
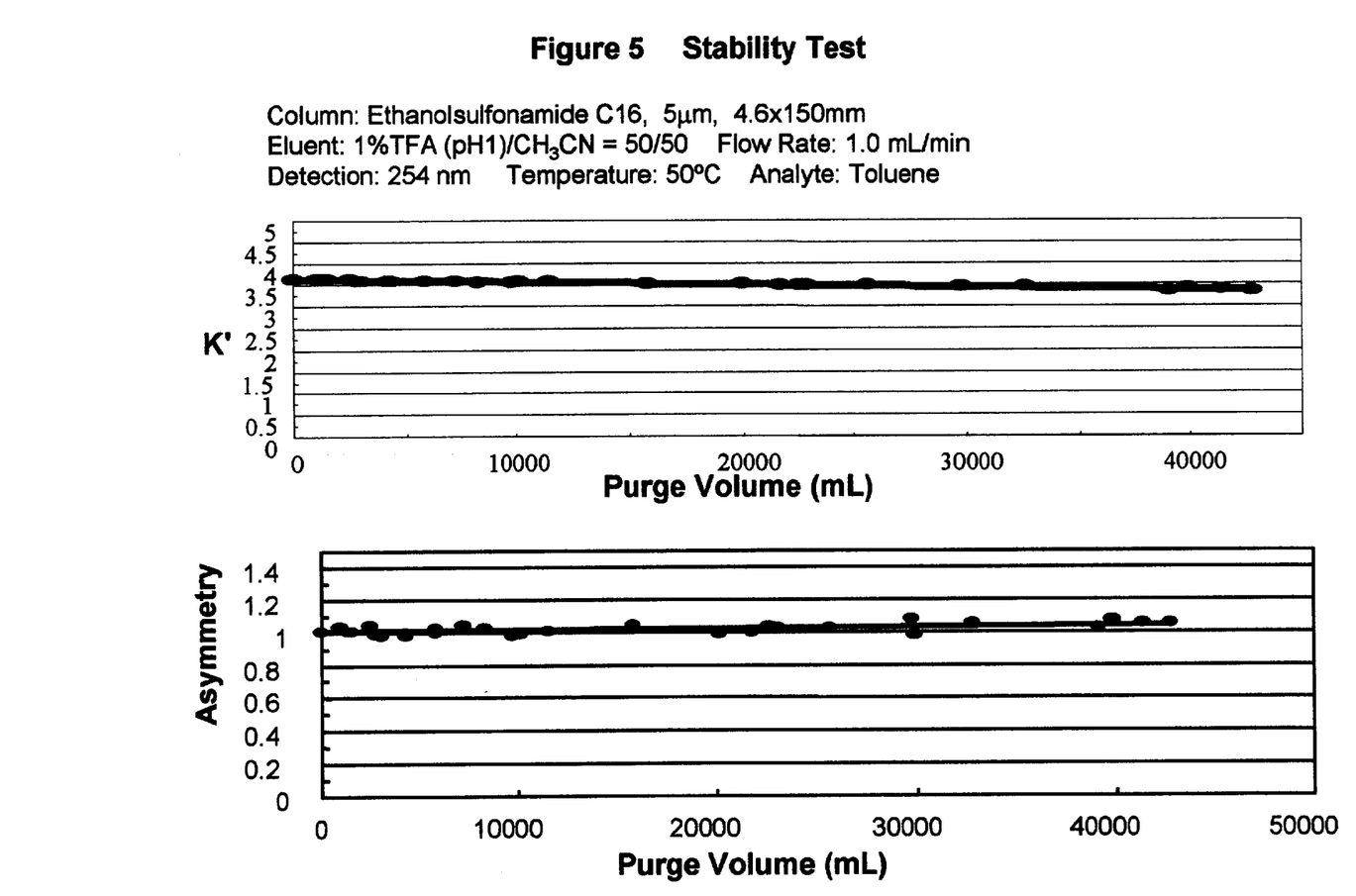
FIG. 5 shows the results of the stability test for ethanolsulfonamide C16 column in pH 1 eluent at 50° C.

FIG. 5 shows the results of the stability test using newly developed ethanolsulfonamide C16 phase under extremely harsh conditions. The test conditions: 50° C., 1% TFA (pH=1) CH$_3$CN/Water, 50/50, continuous flow, 1 mL/min, 5 µL injection volume, 254 nm, analyte: toluene. Both k' and efficiency numbers for toluene do not change during 40L or eluent purge.

EXAMPLE 8

Polar Selectivity Test

Figure 6:
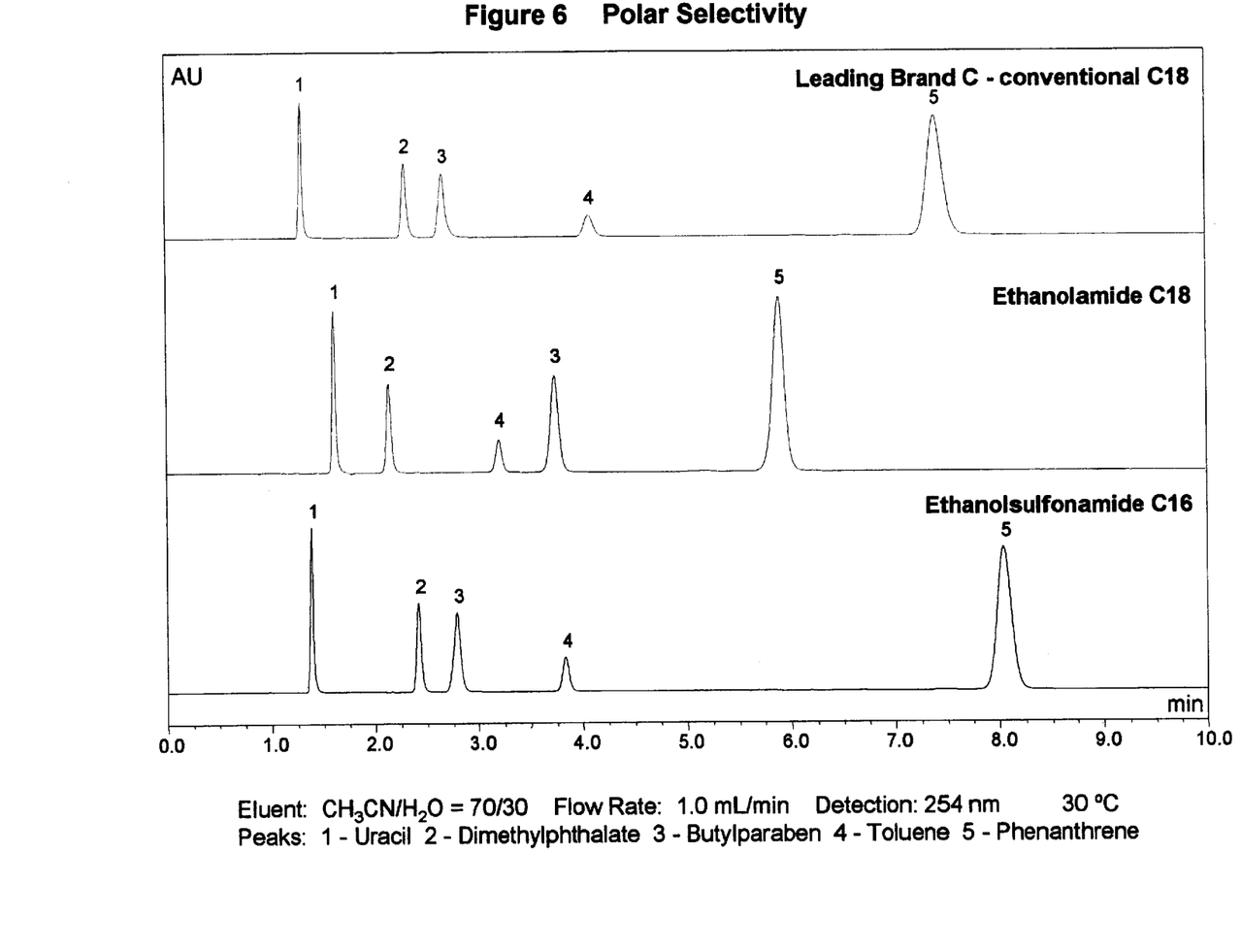
FIG. 6 shows the results of the polar selectivity test for conventional C18 phase and developed ethanolsulfonamide C16 and ethanolamide C18 polar phases. The new ethanolsulfonamide C16 column has similar selectivity to conventional C18 phase while the ethanolamide based material shows reversed order of elution for toluene and butylparaben analytes.

FIG. 6 shows the results of the polar selectivity test for a conventional RP C18 column and the invented ethanolsulfonamide C16 and ethanolamide C18 polar-embedded phases. The test mix is a mixture of uracil, dimethylphthalate, butylparaben, toluene and phenanthrene. It has been shown that the ethanolsulfonamide C16 phase has similar selectivity to conventional RP C18 materials while the ethanolamide phase exhibits different order of elution for toluene and butylparaben analytes. The test conditions: 30° C., 70% CH$_3$CN, 1 mL/min, 5 µL injection volume, 254 nm.

Conclusions Based on the Experiments

The modified silica support with embedded phases according to the invention exhibit decreased interaction with basic analytes due to shielding effect of the polar groups on silica surface. Therefore, the silanol activity is extremely low. Compared with prior art polar-embedded phases and conventional C18 phases, the pyridine peak in unbuffered eluent has the lowest tailing factor and highest efficiency on newly developed ethanolsulfonamide C16 phase (FIG. 1). The peak shape for amitriptyline is excellent on both ethanolsulfonamide and ethanolamide columns at pH 7 (FIG. 2). Both these supports also provide excellent peak characteristics for acids (FIG. 3).

Also, the modified stationary phases of the silica supports have excellent chromatographic properties when used in 100% aqueous media. After 200 hours of continuous exposure to 100% water, the ethanolsulfonamide C16 gave reproducible result, while a conventional RP C18 column collapsed within less than 24 hours (FIG. 4).

The enhanced chemical stability of sulfonamide functional group is another advantage of these invented silica materials. The ethanolsulfonamide fragments of silane ligands in Table 1 have superior resistance towards hydrolysis as compared to conventional amides and carbamates used in the field. Greene, T. W.; Wuts, P. G. M. *Protective Groups in Organic Synthesis* (2$^{nd}$ Edition), John Wiley & Sons (1991). This statement is supported by stability data obtained at pH 1, 50° C. The toluene retention and its peak asymmetry remain unchanged on ethanolsulfonamide C16 phase. The C16 polar-embedded phase has also provided excellent peak shape and good efficiency after 30 days of continuous flow under these harsh conditions.

The synthetic strategy of this invention facilitates the conversion of the aminoalcohols into new surface modifying agents containing various polar functionalities. The diversity of this method leads to several classes of novel polar-embedded phases with variable selectivity that may suit specific chromatographic applications. It has been demonstrated that ethanolsulfonamide C16 polar-embedded phase exhibits similar selectivity to conventional RP C18 column while the ethanolamide C18 phase has different order of elution as shown in FIG. 4.

What is claimed is:

1. A modified silica Support having a a polar phase bound to its surface and suitable for use for chromatographic separations, said modified silica support having the following formula:

wherein, m=0–20; n=0–20; p=1–50;

X is sulfonyl, carbonyl, carbamoyl or oxycarbonyl;

$R_1$=H, alkyl, substituted alkyl, aryl or substituted aryl groups;

$R_2$=alkyl, substituted alkyl, aryl, or substituted aryl groups; and $R_3$ and $R_4$ are alkyl, aryl, hydroxyl, or alkoxyl groups, or groups including oxygen atoms cross-linked to silicon atoms.

2. The modified silica support of claim 1 in which $R_1$ or $R_2$ are C1 to C30 alkyl group.

3. The modified silica support of claim 1 in which $R_1$ or $R_2$ are carbon chains of sufficient length to impart an ion; exchange, ligand exchange, hydrophilic or reverse phase property to the modified silica support.

4. The modified silica support of claim 1 in which X is sulfonyl.

5. The modified silica a support of claim 1 in which p is at least 1.

6. The modified silica support of claim 1 in which at least some of the hydroxyl groups on the silica surface are end-capped by non-polar and/or polar groups.

* * * * *

UNITED STATES PATENT AND TRADEMARK OFFICE
CERTIFICATE OF CORRECTION

PATENT NO.   : 6,645,378 B1
DATED        : November 11, 2003
INVENTOR(S)  : Xiaodong Liu et al.

It is certified that error appears in the above-identified patent and that said Letters Patent is hereby corrected as shown below:

Column 4,
Line 32, delete "f" and insert -- for --; and delete "n 0" and insert -- n=0 --.

Column 13,
Line 5, change "Support to -- support --.

Signed and Sealed this

Eighth Day of June, 2004

JON W. DUDAS
*Acting Director of the United States Patent and Trademark Office*